(12) United States Patent
Kim

(10) Patent No.: US 11,047,843 B2
(45) Date of Patent: Jun. 29, 2021

(54) ATMOSPHERIC ENVIRONMENT MONITORING APPARATUS DETECTING FAILURE OF ATMOSPHERIC ENVIRONMENT SENSOR, AND METHOD FOR DETECTING FAILURE OF ATMOSPHERIC ENVIRONMENT SENSOR

(71) Applicant: SmartCityGrid Co., Ltd., Incheon (KR)

(72) Inventor: Se Kyu Kim, Incheon (KR)

(73) Assignee: SmartCityGrid Co., Ltd., Incheon (KR)

(*) Notice: Subject to any disclaimer, the term of this patent is extended or adjusted under 35 U.S.C. 154(b) by 299 days.

(21) Appl. No.: 16/174,298

(22) Filed: Oct. 30, 2018

(65) Prior Publication Data

US 2019/0195845 A1 Jun. 27, 2019

(30) Foreign Application Priority Data

| Dec. 21, 2017 | (KR) | 10-2017-0177103 |
| Dec. 21, 2017 | (KR) | 10-2017-0177118 |
| Dec. 21, 2017 | (KR) | 10-2017-0177136 |
| Dec. 21, 2017 | (KR) | 10-2017-0177369 |
| Jan. 31, 2018 | (KR) | 10-2018-0011782 |
| Jan. 31, 2018 | (KR) | 10-2018-0011788 |
| Jan. 31, 2018 | (KR) | 10-2018-0011790 |

(51) Int. Cl.
*G01N 33/00* (2006.01)

(52) U.S. Cl.
CPC ....... *G01N 33/007* (2013.01); *G01N 33/0031* (2013.01); *G01N 33/0075* (2013.01); *G01N 33/004* (2013.01); *G01N 33/0047* (2013.01)

(58) Field of Classification Search
CPC ............ G01N 33/007; G01N 33/0031; G01N 33/0075; G01N 33/004; G01N 33/0047
See application file for complete search history.

(56) References Cited

U.S. PATENT DOCUMENTS

| 2003/0033848 | A1* | 2/2003 | Peng | G01N 27/4163 73/1.06 |
| 2006/0155486 | A1* | 7/2006 | Walsh | G01N 33/0034 702/32 |
| 2006/0173580 | A1* | 8/2006 | Desrochers | G01N 33/0075 700/276 |
| 2014/0288780 | A1* | 9/2014 | Berndt | B60R 21/013 701/45 |
| 2015/0077737 | A1* | 3/2015 | Belinsky | G08B 17/107 356/51 |
| 2017/0193788 | A1* | 7/2017 | Kim | G08B 21/14 |
| 2018/0149383 | A1* | 5/2018 | Martin | G01N 33/0075 |

* cited by examiner

*Primary Examiner* — Alexander Satanovsky
*Assistant Examiner* — Lyudmila Zaykova-Feldman
(74) *Attorney, Agent, or Firm* — Revolution IP, PLLC

(57) ABSTRACT

An atmospheric environment monitoring apparatus includes: a communication interface unit which sequentially receives first atmospheric environment measurement data to N-th atmospheric environment measurement data from any one atmospheric environment sensor when a measurement period of an atmospheric environment sensor comes; a data storage unit which stores the first atmospheric environment measurement data to the N-th (N is an integer of 1 or more) atmospheric environment measurement data; and a control unit which checks the total number of the first atmospheric environment measurement data to the N-th atmospheric environment measurement data.

6 Claims, 4 Drawing Sheets

ATMOSPHERIC ENVIRONMENT MONITORING APPARATUS DETECTING FAILURE OF ATMOSPHERIC ENVIRONMENT SENSOR, AND METHOD FOR DETECTING FAILURE OF ATMOSPHERIC ENVIRONMENT SENSOR

BACKGROUND OF THE INVENTION

Field of the Invention

The present invention relates to a technique of detecting failure of an atmospheric environment sensor, and more specifically, to an atmospheric environment monitoring apparatus which detects failure of an atmospheric environment sensor and a method for detecting failure of an atmospheric environment sensor.

Description of the Related Art

In recent, the public's interest for indoor and outdoor atmospheric environment is growing due to frequent occurrence of yellow dust, increase in fine dust concentration, sick house syndrome, and the like.

Because of this, an atmospheric environment measuring system for measuring indoor and outdoor atmospheric environment is also attracting public attention.

Such an atmospheric environment measuring system may include a plurality of atmospheric environment sensors (VOC (volatile organic compound) sensor), carbon monoxide sensor, carbon dioxide sensor, dust sensor, etc.) which measure various kinds of pollutants (for example, volatile organic compound, carbon monoxide, carbon dioxide, fine dust, etc.) and the like existing indoors and outdoors, and an atmospheric environment monitoring apparatus which receives various kinds of atmospheric environment measurement data from the plurality of atmospheric environment sensors and guides an atmospheric environment condition of an indoor or outdoor space.

Herein, the atmospheric environment measuring system may be embodied in a one-body type in which a plurality of atmospheric environment sensors, an atmospheric environment monitoring apparatus, and the like are installed in one body, or may be embodied in a separation type in which a plurality of atmospheric environment sensors, an atmospheric environment monitoring apparatus, and the like are separated from each other.

When a measurement period of a plurality of atmospheric environment sensors comes, each of the plurality of atmospheric environment sensors repeats measurement and transmission for atmospheric environment of an indoor or outdoor space several times, and the atmospheric environment monitoring apparatus sequentially receives a plurality of atmospheric environment measurement data from the plurality of atmospheric environment sensors, calculates an average value thereof, and then may guide an atmospheric environment condition of the indoor or outdoor space by using the average value. The atmospheric environment measuring system described above has to accurately guide atmospheric environment quality of an indoor or outdoor space to a system user.

However, when any one of the plurality of atmospheric environment sensors malfunction, reliability of the whole atmospheric environment management system may decrease. Accordingly, it is urgent to prepare a plan for accurately determining failure of each of the plurality of atmospheric environment sensors.

SUMMARY OF THE INVENTION

The invention provides an apparatus and a method which check the total number of atmospheric environment measurement data sequentially received from atmospheric sensors when a measurement period of the atmospheric environment sensors comes, determine that failure occurred in the atmospheric environment sensors when the total number of atmospheric environment measurement data is equal to or less than M, check the number of atmospheric environment measurement data including an abnormal measurement value of the plurality of atmospheric environment measurement data sequentially received from the atmospheric environment sensors when the total number of atmospheric environment measurement data is more than M, and determine that failure occurred in the atmospheric environment sensors even when the number of atmospheric environment measurement data including an abnormal measurement value is equal to or more than a predetermined number.

The invention provides an apparatus and a method which classify atmospheric environment measurement data measured by atmospheric environment sensors of an environment measuring system into a plurality of data groups in accordance with correlation to each other, determine data validity by data groups including two or more atmospheric environment data with correlation, and determine that failure occurred in one or more atmospheric environment sensors of the plurality of atmospheric environment sensors when there are one or more invalid data groups.

According to an aspect of the invention, an atmospheric environment monitoring apparatus which detects failure of an atmospheric environment sensor is provided.

An atmospheric environment monitoring apparatus which detects failure of an atmospheric environment sensor according to a first embodiment of the invention includes: a communication interface unit which sequentially receives first atmospheric environment measurement data to N-th atmospheric environment measurement data from any one atmospheric environment sensor when a measurement period of an atmospheric environment sensor comes; a data storage unit which stores the first atmospheric environment measurement data to the N-th (N is an integer of 2 or more) atmospheric environment measurement data; and a control unit which checks the total number of the first atmospheric environment measurement data to the N-th atmospheric environment measurement data, primarily determines that failure occurred in the atmospheric environment sensor when the total number is equal to or less than M (M is an integer of 2 or more), checks the number of abnormal atmospheric environment measurement data which are atmospheric environment measurement data including an abnormal atmospheric environment measurement value of the first atmospheric environment measurement to the N-th atmospheric environment measurement data when the total number is more than M, and secondarily determines that failure occurred in the atmospheric environment sensor even when the number of abnormal atmospheric environment measurement data is equal to or more than a predetermined number.

An atmospheric environment monitoring apparatus which detects failure of an atmospheric environment sensor according to a second embodiment of the invention includes: a communication interface unit which periodically receives first atmospheric environment measurement data to N-th atmospheric environment measurement data from a first atmospheric environment sensor to an N-th atmospheric environment sensor; a data storage unit which cumulates and stores the first atmospheric environment measurement data to the N-th atmospheric environment measurement data periodically received from the first atmospheric environment sensor to the N-th atmospheric environment sensor by the communication interface unit; and a control unit which classifies the first atmospheric environment measurement data to the N-th atmospheric environment measurement data into a first correlation data group to an L-th correlation data group, determines data validity for each of the first correlation data group to the L-th correlation data group, and determines that failure occurred in one or more atmospheric environment sensors of the first atmospheric environment sensor to the N-th atmospheric environment sensor when there are one or more invalid correlation data groups of the first correlation data group to the L-th correlation data group.

According to another aspect of the invention, a method for detecting failure of an atmospheric environment sensor is provided.

A method for detecting failure of an atmospheric environment sensor according to a first embodiment of the invention includes: a data reception step of sequentially receiving first atmospheric environment measurement data to N-th (N is an integer of 1 or more) atmospheric environment measurement data from any one atmospheric environment sensor when a measurement period of an atmospheric environment sensor comes; a data storage step of storing the first atmospheric environment measurement data to the N-th atmospheric environment measurement data; a data number check step of checking the total number of the first atmospheric environment measurement data to the N-th atmospheric environment measurement data; a primary failure determination step of determining that failure occurred in the atmospheric environment sensor when the total number of is equal to or less than M (M is an integer of 2 or more); an abnormal measurement data number check step of checking the number of abnormal atmospheric environment measurement data which are atmospheric environment measurement data including an abnormal atmospheric environment measurement value of the first atmospheric environment measurement to the N-th atmospheric environment measurement data when the total number is more than M; and a secondary failure determination step of determining that failure occurred in the atmospheric environment sensor even when the number of abnormal atmospheric environment measurement data is equal to or more than a predetermined number.

A method for detecting failure of an atmospheric environment sensor according to a second embodiment of the invention includes: a data reception step of periodically receiving first atmospheric environment measurement data to N-th atmospheric environment measurement data from a first atmospheric environment sensor to an N-th atmospheric environment sensor; a data classification step of classifying the first atmospheric environment measurement data to the N-th atmospheric environment measurement data into a first correlation data group to an L-th correlation data group in accordance with correlation to each other; a validity determination step of determining data validity for each of the first correlation data group to the L-th correlation data group; and a sensor failure detection step of determining that failure occurred in one or more atmospheric environment sensors of the first atmospheric environment sensor to the N-th atmospheric environment sensor when there are one or more invalid correlation data groups of the first correlation data group to the L-th correlation data group, as a result of determination of data validity for each of the first correlation data group to the L-th correlation data group.

DETAILED DESCRIPTION OF THE PREFERRED EMBODIMENTS

Figure 1:
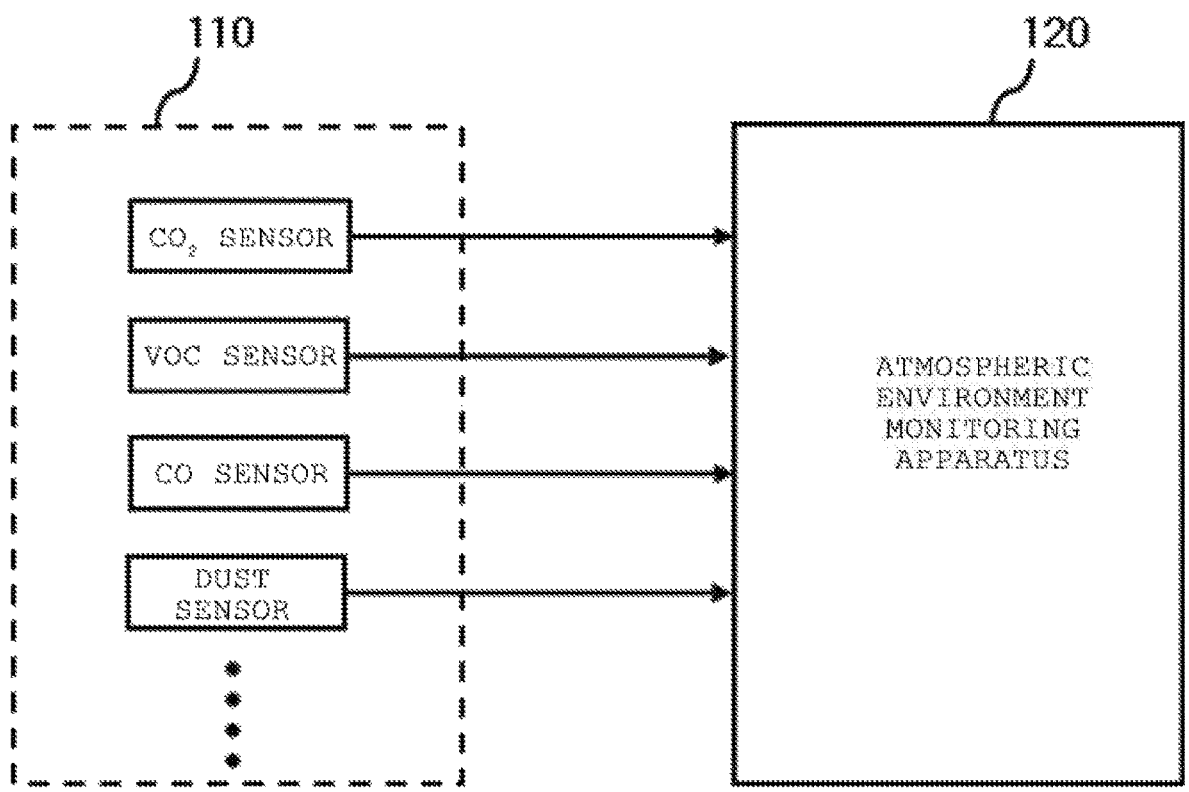
FIG. 1 is a diagram schematically illustrating a configuration of an atmospheric environment measuring system according to an embodiment of the invention.

Hereinafter, the invention will be described with reference to the accompanying drawings. However, the invention may be embodied in various different forms, and is not limited to embodiments described herein. In the drawings, in order to clearly describe the invention, parts unrelated to the description are omitted, and similar reference numerals and signs are given to similar parts throughout Specification.

FIG. 1 is a diagram schematically illustrating a configuration of an atmospheric environment measuring system according to an embodiment of the invention.

Referring to FIG. 1, an atmospheric environment measuring system 100 includes a first atmospheric environment sensor to an N-th atmospheric environment sensor 110, and an atmospheric environment monitoring apparatus 120.

The first atmospheric environment sensor to the N-th atmospheric environment sensor 110 may include a VOC (volatile organic compound) sensor, a carbon monoxide sensor, a carbon dioxide sensor, and a fine dust sensor.

Such a first atmospheric environment sensor to N-th atmospheric environment sensor 110 is installed in an indoor or outdoor space of a predetermined area, measures an atmospheric environment condition of the predetermined area, that is, periodically measures volatile organic compound concentration, carbon monoxide concentration, carbon dioxide concentration, fine dust concentration, and the like, and may periodically generate and transmit first atmospheric environment measurement data to N-th atmospheric environment measurement data, which are measurement data for each of these, to an atmospheric environment monitoring apparatus 120.

Specifically, the VOC sensor included in the first atmospheric environment sensor to the N-th atmospheric environment sensor 110 periodically measures VOC concentration of a predetermined area, and may generate and transmit VOC concentration data, which is atmospheric environment measurement data for this, to the atmospheric environment monitoring apparatus 120.

In addition, the carbon monoxide sensor included in the first atmospheric environment sensor to the N-th atmospheric environment sensor 110 periodically measures carbon monoxide concentration of a predetermined area, and may generate and transmit carbon monoxide concentration data, which is atmospheric environment measurement data for this, to the atmospheric environment monitoring apparatus 120.

In addition, the carbon dioxide sensor included in the first atmospheric environment sensor to the N-th atmospheric environment sensor 110 periodically measures carbon dioxide concentration of a predetermined area, and may generate and transmit carbon dioxide concentration data, which is atmospheric environment measurement data for this, to the atmospheric environment monitoring apparatus 120.

In addition, the fine dust sensor included in the first atmospheric environment sensor to the N-th atmospheric environment sensor 110 periodically measures fine dust concentration of a predetermined area, and may generate and transmit fine dust concentration data, which is atmospheric environment measurement data for this, to the atmospheric environment monitoring apparatus 120.

In the first atmospheric environment sensor to the N-th atmospheric environment sensor 110 described above, all operation (measurement, generation, and transmission) periods of the first atmospheric environment sensor to the N-th atmospheric environment sensor 110 may be set equally or similarly in order to secure accuracy among the atmospheric environment measurement data.

The atmospheric environment monitoring apparatus 120 periodically receives the first atmospheric environment measurement data to the N-th atmospheric environment measurement data from the first atmospheric environment sensor to the N-th atmospheric environment sensor 110, and determines and guides an outdoor atmospheric environment condition of a predetermined area.

Herein, the atmospheric environment monitoring apparatus 120 may be formed in a one-body type or separation type with respect to the first atmospheric environment sensor to the N-th environment sensor 110.

When the atmospheric environment monitoring apparatus 120 is formed in the separation type with respect to the first atmospheric environment sensor to the N-th atmospheric environment senor 110, the atmospheric environment monitoring apparatus 120 may receive the first atmospheric environment measurement data to the N-th atmospheric environment measurement data from the first atmospheric environment sensor to the N-th atmospheric environment sensor 110 through short-range wireless communication, cable communication, and Internet communication via the Internet network with the first atmospheric environment sensor to the N-th atmospheric environment sensor 110.

In the first embodiment of the invention, if failure occurred in any one atmospheric environment sensor 112, the number of atmospheric environment measurement data successful in transmission to the atmospheric environment monitoring apparatus 120 may be equal to or less than a predetermined number when any one atmospheric environment sensor 112 transmits a plurality of atmospheric environment measurement data to the atmospheric environment monitoring apparatus 120.

In addition, even when the number of atmospheric environment measurement data successful in transmission to the atmospheric environment monitoring apparatus 120 is more than the predetermined number, a predetermined number or more of atmospheric environment measurement data including an abnormal measurement value may be transmitted to the atmospheric environment monitoring apparatus 120.

It is obvious that a symptom when failure occurred in any one atmospheric environment sensor 112 as described above may appear even in other atmospheric environment sensors included in the plurality of atmospheric environment sensors 110.

In the embodiment of the invention, the atmospheric environment monitoring apparatus 120 may determine failure which may occur in any one atmospheric environment sensor 112 as described above.

In other words, the atmospheric environment monitoring apparatus 120 may determine failure which may occur in each of one or more atmospheric environment sensors of the plurality of atmospheric environment sensors 110.

Hereinafter, for convenience of description, only a process in which the atmospheric environment monitoring apparatus 120 determines failure for any one atmospheric environment sensor 112 is described, but it is obvious that the process of determining failure according to the embodiment of the invention may be applied to each of the plurality of atmospheric environment sensors 110.

When a measurement period of the atmospheric environment sensor comes, the atmospheric environment monitoring apparatus 120 sequentially receives and stores first atmospheric environment measurement data to N-th (N is an integer of 1 or more) atmospheric environment measurement data from any one atmospheric environment sensor 112. Herein, the number of first atmospheric environment measurement data to N-th atmospheric environment data may be equal to the number of the plurality of atmospheric environment measurement data generated by repeatedly measuring an atmospheric environment condition of a predetermined area by any one atmospheric environment sensor 112 or may be less than the number of the plurality of atmospheric environment measurement data.

In other words, when any one atmospheric environment sensor 112 is in a normal condition and all the plurality of atmospheric environment measurement data are transmitted to the atmospheric environment monitoring apparatus 120, the total number of first atmospheric environment measurement data to N-th atmospheric environment measurement data may be equal to the number of the plurality of atmospheric environment measurement data.

Meanwhile, when failure occurs in any one atmospheric environment sensor 112 and only a part of the plurality of atmospheric environment measurement data are transmitted to the atmospheric environment monitoring apparatus 120, the total number of first atmospheric environment measurement data to N-th atmospheric environment measurement data may be less than the number of the plurality of atmospheric environment measurement data.

The atmospheric environment monitoring apparatus 120 receiving and storing first atmospheric environment measurement data to the N-th atmospheric environment measurement data checks the total number of the first atmospheric environment measurement data to the N-th atmospheric environment measurement data, and checks whether the total number of first atmospheric environment measurement data to N-th atmospheric environment measurement data is equal to or less than M (M is an integer of 2 or more), which is a preset primary failure determination criterion. Herein, M, which is the failure determination criterion, may be equal to the number of measurement times of any one atmospheric environment sensor 112 or may be less than the number of measurement times.

When the total number of first atmospheric environment measurement data to N-th atmospheric environment measurement data is equal to or less than M, the atmospheric environment monitoring apparatus 120 may primarily determine that failure occurred in any one atmospheric environment sensor 112. In this case, the atmospheric environment monitoring apparatus 120 may generate a failure occurrence guide message which is a message for guiding failure occurrence of any one atmospheric environment sensor 112 to an atmospheric environment measuring system user, and transmit the failure occurrence guide message to a mobile communication terminal of the atmospheric environment measuring system user.

In addition, the atmospheric environment monitoring apparatus 120 may generate a failure occurrence guide message for any one atmospheric environment sensor 112, and may output text for the failure occurrence guide message on a screen or output the failure occurrence guide message by audible tone.

Meanwhile, when the primary failure determination result for any one atmospheric environment sensor 112 is normal, in other words, when the total number of first atmospheric environment measurement data to N-th atmospheric environment measurement data is more than M, the atmospheric environment monitoring apparatus 120 may check the number of abnormal atmospheric environment measurement data which are atmospheric environment measurement data including an abnormal atmospheric environment measurement value of the first atmospheric environment measurement data to the N-th atmospheric environment measurement data.

The atmospheric environment monitoring apparatus 120 checks whether the number of abnormal atmospheric environment measurement data is equal to or more than a predetermined number, which is a preset secondary failure determination criterion.

When the number of abnormal atmospheric environment measurement data is equal to or more than the predetermined number, which is the preset secondary failure determination criterion, the atmospheric environment monitoring apparatus 120 may secondarily determine that failure occurred in any one atmospheric environment sensor 120. In this case, the atmospheric environment monitoring apparatus 120 may generate a failure occurrence guide message which is a message for guiding failure occurrence of any one atmospheric environment sensor 112 to an atmospheric environment measuring system user, and transmit the failure occurrence guide message to a mobile communication terminal of the atmospheric environment measuring system user.

In addition, the atmospheric environment monitoring apparatus 120 may generate a failure occurrence guide message for any one atmospheric environment sensor 112, and may output text for the failure occurrence guide message on a screen or output the failure occurrence guide message by audible tone.

Meanwhile, in the embodiment of the invention, the atmospheric environment monitoring apparatus 120 may calculate an average value of a first atmospheric environment measurement value to an N-th atmospheric environment measurement value included in the first atmospheric environment measurement data to the N-th atmospheric environment measurement data, and may determine, as abnormal atmospheric environment measurement data, each of one or more atmospheric environment measurement data including an atmospheric environment measurement value with a deviation from the average value equal to or more than a predetermined criterion of the first atmospheric environment measurement data to the N-th atmospheric environment measurement data.

In a second embodiment of the invention, an atmospheric environment monitoring apparatus 120 classifies first atmospheric environment measurement data to N-th atmospheric environment measurement data received from a first atmospheric environment sensor to an N-th atmospheric environment sensor 110, in accordance with correlation.

In other words, the atmospheric environment monitoring apparatus 120 classifies the first atmospheric environment measurement data to the N-th atmospheric environment measurement data into a first correlation data group to an L-th correlation data group. Herein, N and L are natural numbers, and L may be less than N. In other words, N and L have a relation of L<N.

For example, when the first atmospheric environment measurement data to the N-th atmospheric environment measurement data include VOC concentration data, carbon monoxide concentration data, carbon dioxide data, and fine dust concentration data, the atmospheric environment monitoring apparatus 120 may classify the carbon monoxide concentration data and the carbon dioxide concentration data having a proportional relation to each other into a first correlation data group, and may classify the VOC concentration data and the fine dust concentration data into a second correlation data group.

More specifically, since it is general that carbon monoxide concentration and carbon dioxide concentration in the indoor or outdoor air increase together in accordance with increase of car exhaust and thermal power generation and use of indoor boiler and heating appliance, the atmospheric environment monitoring apparatus 120 may classify the carbon monoxide concentration data and the carbon dioxide concentration data into the first correlation data group.

Meanwhile, since the volatile organic compound (VOC) is a precursor of fine dust, it is general that fine dust concentration in indoor or outdoor air increases together as VOC concentration in indoor or outdoor air increases. Accordingly, the atmospheric environment monitoring apparatus 120 may classify the VOC concentration data into the second correlation data group.

The atmospheric environment monitoring apparatus 120 which classified the first atmospheric environment measurement data to the N-th atmospheric environment measurement data into the first correlation data group to the L-th correlation data group as described above determines data validity for each of the first correlation data group to the L-th correlation data group.

Herein, a configuration in which the atmospheric environment monitoring apparatus 120 determines data validity for any one correlation data group is as follows.

The atmospheric environment monitoring apparatus 120 receives each of two or more atmospheric environment measurement data included in any one correlation data group during a predetermined period, and identifies a data change pattern during a predetermined period for each of two or more atmospheric environment measurement data.

Herein, when the data change patterns for two or more atmospheric environment measurement data are the same, the atmospheric environment monitoring apparatus 120 may determine that two or more atmospheric environment measurement data included in any one correlation data group are valid, that is, may determine that any one correlation data group is valid.

Meanwhile, when there are one or more data change patterns different from the other data change pattern of data change patterns for two or more atmospheric environment measurement data, the atmospheric environment monitoring apparatus 120 may determine that two or more atmospheric environment measurement data included in any one correlation data group are not valid, that is, may determine that any one correlation data group is not valid.

For example, when all the data change patterns during a predetermined period for carbon monoxide concentration data and carbon dioxide concentration data are an increase pattern or decrease pattern in the first correlation data group including the carbon monoxide concentration data and the carbon dioxide concentration data having a proportional relation to each other, the atmospheric environment monitoring apparatus 120 may determine that the carbon monoxide concentration data and the carbon dioxide concentration data are valid.

Meanwhile, when the data change pattern of the carbon monoxide concentration data is an increase pattern but the data change pattern of the carbon dioxide concentration data is a decrease pattern or invariable, the atmospheric environment monitoring apparatus 120 may determine that any one data of the carbon monoxide concentration data and the carbon dioxide concentration data is not valid.

The atmospheric environment monitoring apparatus 120 may determine data validity for each of the first correlation data group to the L-th correlation data group through such a configuration.

As a result of determination of data validity for each of the first correlation data group to the L-th correlation data group in the atmospheric environment monitoring apparatus 120, when there are one or more invalid correlation data groups of the first correlation data group to the L-th correlation data group, the atmospheric environment monitoring apparatus 120 may determine that failure occurred in one or more atmospheric environment sensors of the first atmospheric environment sensor to the N-th atmospheric environment sensor 110.

In such a case, the atmospheric environment monitoring apparatus 120 may generate an atmospheric environment sensor check requirement message, which is a message for guiding check necessity of the one or more atmospheric environment sensor to an environment measuring system manager, and transmit the message to a mobile communication terminal of the environment measuring system manager.

Hereinafter, a configuration of the atmospheric environment monitoring apparatus 120 according to an embodiment of the invention will be described.

Figure 2:
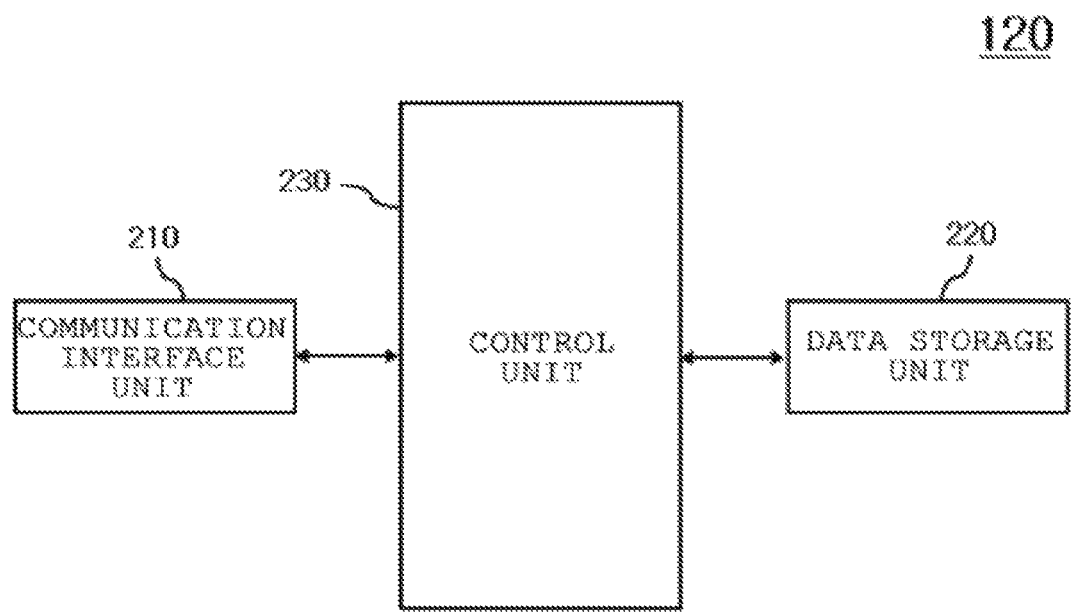
FIG. 2 is a diagram schematically illustrating a configuration of an atmospheric environment monitoring apparatus according to an embodiment of the invention.

FIG. 2 is a block diagram schematically illustrating a configuration of an atmospheric environment monitoring apparatus according to an embodiment of the invention.

The atmospheric environment monitoring apparatus 120 according to an embodiment of the invention may include a communication interface unit 210, a data storage unit 220, and a control unit 230.

In addition, the atmospheric environment monitoring apparatus 120 may further include a failure occurrence guide unit (not illustrated) which outputs a failure occurrence guide message for failure occurrence of an atmospheric environment sensor by any one of text and audible tone. Herein, the failure occurrence guide unit (not illustrated) may include one or more of a display module and a speaker module.

The communication interface unit 210 may periodically receive first atmospheric environment measurement data to N-th atmospheric environment measurement data from a first atmospheric environment sensor to an N-th atmospheric environment sensor 110 through any one of short-range wireless communication, cable communication, and Internet communication via the Internet communication network with the first atmospheric environment sensor to the N-th atmospheric environment sensor 110.

In addition, the communication interface unit 210 may transmit an atmospheric environment sensor check requirement message, which is a message for guiding check necessity of the one or more atmospheric environment sensor to an environment measuring system manager of the first atmospheric environment sensor to the N-th atmospheric environment sensor 110, to a mobile communication terminal of an environment measuring system manager. Herein, it is obvious that the communication interface unit 210 may transmit the atmospheric environment sensor check requirement message to the mobile communication terminal of the environment measuring system manager through a mobile communication network.

Such a communication interface unit 210 may include one or more of a short-range wireless communication module and a network interface card.

The data storage unit 220 temporarily stores data processed by a control unit 230 to be described later, stores a program for performing a function of the atmospheric environment monitoring apparatus 120, and stores data necessary for operation of the atmospheric environment monitoring apparatus 120.

In the embodiment of the invention, the data storage unit 220 cumulates and stores first atmospheric environment measurement data to N-th atmospheric environment measurement data which the communication interface unit 210 periodically receives from the first atmospheric environment sensor to the N-th atmospheric environment sensor 110.

Such a data storage unit 220 may be configured by an internal memory device of the atmospheric environment monitoring apparatus 120 or an external storage server and the like.

The control unit 230 is a module providing an overall function of the atmospheric environment monitoring apparatus 120, and may be embodied by a main board of the atmospheric environment monitoring apparatus 120 or the like.

In the first embodiment of the invention, the control unit 230 diversely determines whether failure occurred for any one atmospheric environment sensor 120 as follows.

First, the control unit 230 checks the total number of first atmospheric environment measurement data to N-th atmospheric environment measurement data which the communication interface unit 210 receives from any one atmospheric environment sensor 112, and checks whether the total number is equal to or less than M (M is an integer of 2 or more), which is a preset primary failure determination criterion.

When the total number of first atmospheric environment measurement data to N-th atmospheric environment measurement data is equal to or less than M, the control unit 230 may primarily determine that failure occurred in any one atmospheric environment sensor 112. In this case, the control unit 230 may generate a failure occurrence guide message which is a message for guiding failure occurrence of any one atmospheric environment sensor 112 to an atmospheric environment measuring system user, and transmit the failure occurrence guide message to a mobile communication terminal of the atmospheric environment measuring system user through the communication interface unit 210.

In addition, when the atmospheric environment monitoring apparatus 120 includes a failure occurrence guide unit (not illustrated), the control unit 230 may generate a failure occurrence guide message for any one atmospheric environment sensor 112, and output the failure occurrence guide message for any one atmospheric environment sensor 112 through the failure occurrence guide unit (not illustrated).

When the primary failure determination result for any one atmospheric environment sensor 112 is normal, in other words, when the total number of first atmospheric environment measurement data to N-th atmospheric environment measurement data is more than M, the control unit 230 may check the number of abnormal atmospheric environment measurement data which are atmospheric environment measurement data including an abnormal atmospheric environment measurement value of the first atmospheric environment measurement data to the N-th atmospheric environment measurement data.

The control unit 230 checks whether the number of abnormal atmospheric environment measurement data is equal to or more than a predetermined number, which is a preset secondary failure determination criterion.

When the number of abnormal atmospheric environment measurement data is equal to or more than the predetermined number, which is the preset secondary failure determination criterion, the control unit 230 may secondarily determine that failure occurred in any one atmospheric environment sensor 120. In this case, the control unit 230 may generate a failure occurrence guide message which is a message for guiding failure occurrence of any one atmospheric environment sensor 112 to an atmospheric environment measuring system user, and transmit the failure occurrence guide message to a mobile communication terminal of the atmospheric environment measuring system user through the communication interface unit 210.

In addition, when the atmospheric environment monitoring apparatus 120 includes a failure occurrence guide unit (not illustrated), the control unit 230 may generate a failure occurrence guide message for any one atmospheric environment sensor 112, and output the failure occurrence guide message for any one atmospheric environment sensor 112 through the failure occurrence guide unit (not illustrated).

Meanwhile, the control unit 230 in the embodiment of the invention may calculate an average value of a first atmospheric environment measurement value to an N-th atmospheric environment measurement value included in the first atmospheric environment measurement data to the N-th atmospheric environment measurement data, and may determine, as abnormal atmospheric environment measurement data, each of one or more atmospheric environment measurement data including an atmospheric environment measurement value with a deviation from the average value equal to or more than a predetermined criterion of the first atmospheric environment measurement data to the N-th atmospheric environment measurement data.

As described above, in the embodiment of the invention, the atmospheric environment monitoring apparatus 120 diversely determines whether failure of an atmospheric environment sensor occurred, the atmospheric environment monitoring apparatus 120 can accurately determine failure for each of a plurality of atmospheric environment sensors 110.

In the second embodiment of the invention, the control unit 230 classifies first atmospheric environment measurement data to N-th atmospheric environment measurement data which the communication interface unit 210 receives from the first atmospheric environment sensor to the N-th atmospheric environment sensor 110, in accordance with correlation.

In other words, the control unit 230 classifies the first atmospheric environment measurement data to the N-th atmospheric environment measurement data into a first correlation data group to an L-th correlation data group.

For example, when the first atmospheric environment measurement data to the N-th atmospheric environment measurement data include VOC concentration data, carbon monoxide concentration data, carbon dioxide data, and fine dust concentration data, the control unit 230 may classify the carbon monoxide concentration data and the carbon dioxide concentration data having a proportional relation to each other into a first correlation data group, and may classify the VOC concentration data and the fine dust concentration data into a second correlation data group.

More specifically, since it is general that carbon monoxide concentration and carbon dioxide concentration in the indoor or outdoor air increase together in accordance with increase of car exhaust and thermal power generation and use of indoor boiler and heating appliance, the control unit 230 may classify the carbon monoxide concentration data and the carbon dioxide concentration data into the first correlation data group.

Meanwhile, since the volatile organic compound (VOC) is a precursor of fine dust, it is general that fine dust concentration in indoor or outdoor air increases together as VOC concentration in indoor or outdoor air increases. Accordingly, the control unit 230 may classify the VOC concentration data into the second correlation data group.

The control unit 230 which classified the first atmospheric environment measurement data to the N-th atmospheric environment measurement data into the first correlation data group to the L-th correlation data group as described above determines data validity for each of the first correlation data group to the L-th correlation data group.

Herein, a configuration in which the control unit 230 determines data validity for any one correlation data group is as follows.

The control unit 230 extracts two or more atmospheric environment measurement data included in any one correlation data group of the first atmospheric environment measurement data to the N-th atmospheric environment measurement data cumulated and stored in the data storage unit 220, and identifies a data change pattern during a predetermined period for each of two or more atmospheric environment measurement data.

Herein, when the data change patterns for two or more atmospheric environment measurement data are the same, the control unit 230 may determine that two or more atmospheric environment measurement data included in any one correlation data group are valid, that is, may determine that any one correlation data group is valid.

Meanwhile, when there are one or more data change patterns different from the other data change pattern of data change patterns for two or more atmospheric environment measurement data, the control unit 230 may determine that two or more atmospheric environment measurement data included in any one correlation data group are not valid, that is, may determine that any one correlation data group is not valid.

For example, when all the data change patterns during a predetermined period for carbon monoxide concentration data and carbon dioxide concentration data are an increase pattern or decrease pattern in the first correlation data group including the carbon monoxide concentration data and the carbon dioxide concentration data having a proportional relation to each other, the control unit 230 may determine that the carbon monoxide concentration data and the carbon dioxide concentration data are valid.

Meanwhile, when the data change pattern of the carbon monoxide concentration data is an increase pattern but the data change pattern of the carbon dioxide concentration data is a decrease pattern or invariable, the control unit 230 may determine that any one data of the carbon monoxide concentration data and the carbon dioxide concentration data is not valid.

The control unit 230 may determine data validity for each of the first correlation data group to the L-th correlation data group through such a configuration.

As a result of determination of data validity for each of the first correlation data group to the L-th correlation data group in the control unit 230, when there are one or more invalid correlation data groups of the first correlation data group to the L-th correlation data group, the control unit 230 may determine that failure occurred in one or more atmospheric environment sensors of the first atmospheric environment sensor to the N-th atmospheric environment sensor 110.

In such a case, the control unit 230 may generate an atmospheric environment sensor check requirement message which is a message for guiding check necessity of the one or more atmospheric environment sensor to an environment measuring system manager, and transmit the atmospheric environment sensor check requirement message to a mobile communication terminal of the environment measuring system manager through the communication interface unit 210.

As described above, in the embodiment of the invention, the atmospheric environment monitoring apparatus 120 classifies atmospheric environment measurement data received from a plurality of atmospheric environment sensors into a plurality of data groups in accordance with correlation to each other, determine data validity by data groups including two or more atmospheric environment data with correlation, and may determine that failure occurred in one or more atmospheric environment sensors of the plurality of atmospheric environment sensors when there are one or more invalid data groups. Accordingly, it is possible to determine failure of the atmospheric environment sensors more simply as compared with determining failure for each of atmospheric environment sensors in the related art.

Hereinafter, a process in which the atmospheric environment monitoring apparatus 120 according to the embodiment of the invention detects failure of an atmospheric environment sensor will be described.

Figure 3:
FIG. 3 is a flowchart illustrating a process in which an atmospheric environment monitoring apparatus according to a first embodiment of the invention detects failure of an atmospheric environment sensor.

FIG. 3 is a flowchart illustrating a process in which an atmospheric environment monitoring apparatus according to the first embodiment of the invention detects failure of an atmospheric environment sensor.

When a measurement period of the atmospheric environment sensor comes, the atmospheric environment monitoring apparatus 120 sequentially receives and stores first atmospheric environment measurement data to N-th (N is an integer of 1 or more) atmospheric environment measurement data from any one atmospheric environment sensor 112 (S310).

The atmospheric environment monitoring apparatus 120 receiving and storing first atmospheric environment measurement data to the N-th atmospheric environment measurement data checks the total number of the first atmospheric environment measurement data to the N-th atmospheric environment measurement data, and checks whether the total number of first atmospheric environment measurement data to N-th atmospheric environment measurement data is equal to or less than M (M is an integer of 2 or more), which is a preset primary failure determination criterion (S320, S330).

When the total number of first atmospheric measurement data to N-th atmospheric environment measurement data is equal to or less than M, the atmospheric environment monitoring apparatus 120 may primarily determine that failure occurred in any one atmospheric environment sensor 112 (S340).

In this case, the atmospheric environment monitoring apparatus 120 may generate a failure occurrence guide message which is a message for guiding failure occurrence of any one atmospheric environment sensor 112 to an atmospheric environment measuring system user, and transmit the failure occurrence guide message to a mobile communication terminal of the atmospheric environment measuring system user.

In addition, the atmospheric environment monitoring apparatus 120 may generate a failure occurrence guide message for any one atmospheric environment sensor 112, and output text for the failure occurrence guide message on a screen or output the failure occurrence guide message by audible tone.

Meanwhile, in Step S330, when the total number of first atmospheric environment measurement data to N-th atmospheric environment measurement data is more than M, the atmospheric environment monitoring apparatus 120 may check the number of abnormal atmospheric environment measurement data which are atmospheric environment measurement data including an abnormal atmospheric environment measurement value of the first atmospheric environment measurement data to the N-th atmospheric environment measurement data (S350).

The atmospheric environment monitoring apparatus 120 checks whether the number of abnormal atmospheric environment measurement data is equal to or more than a predetermined number, which is a preset secondary failure determination criterion (S360).

When the number of abnormal atmospheric environment measurement data is equal to or more than the predetermined number, which is the preset secondary failure determination criterion, the atmospheric environment monitoring apparatus 120 may secondarily determine that failure occurred in any one atmospheric environment sensor 120 (S370). In this case, the atmospheric environment monitoring apparatus 120 may generate a failure occurrence guide message which is a message for guiding failure occurrence of any one atmospheric environment sensor 112 to an atmospheric environment measuring system user, and transmit the failure occurrence guide message to a mobile communication terminal of the atmospheric environment measuring system user.

In addition, the atmospheric environment monitoring apparatus 120 may generate a failure occurrence guide message for any one atmospheric environment sensor 112, and output text for the failure occurrence guide message on a screen or output the failure occurrence guide message by audible tone.

In Step S360, when the number of abnormal atmospheric environment measurement data is equal to or less than a predetermined number, the atmospheric environment monitoring apparatus 120 may determine that a condition of any one atmospheric environment sensor 112 is normal (S380).

In Step S350, the atmospheric environment monitoring apparatus 120 may calculate an average value of a first atmospheric environment measurement value to an N-th atmospheric environment measurement value included in the first atmospheric environment measurement data to the N-th atmospheric environment measurement data, and may determine, as abnormal atmospheric environment measurement data, each of one or more atmospheric environment measurement data including an atmospheric environment measurement value with a deviation from the average value equal to or more than a predetermined criterion of the first atmospheric environment measurement data to the N-th atmospheric environment measurement data.

Figure 4:
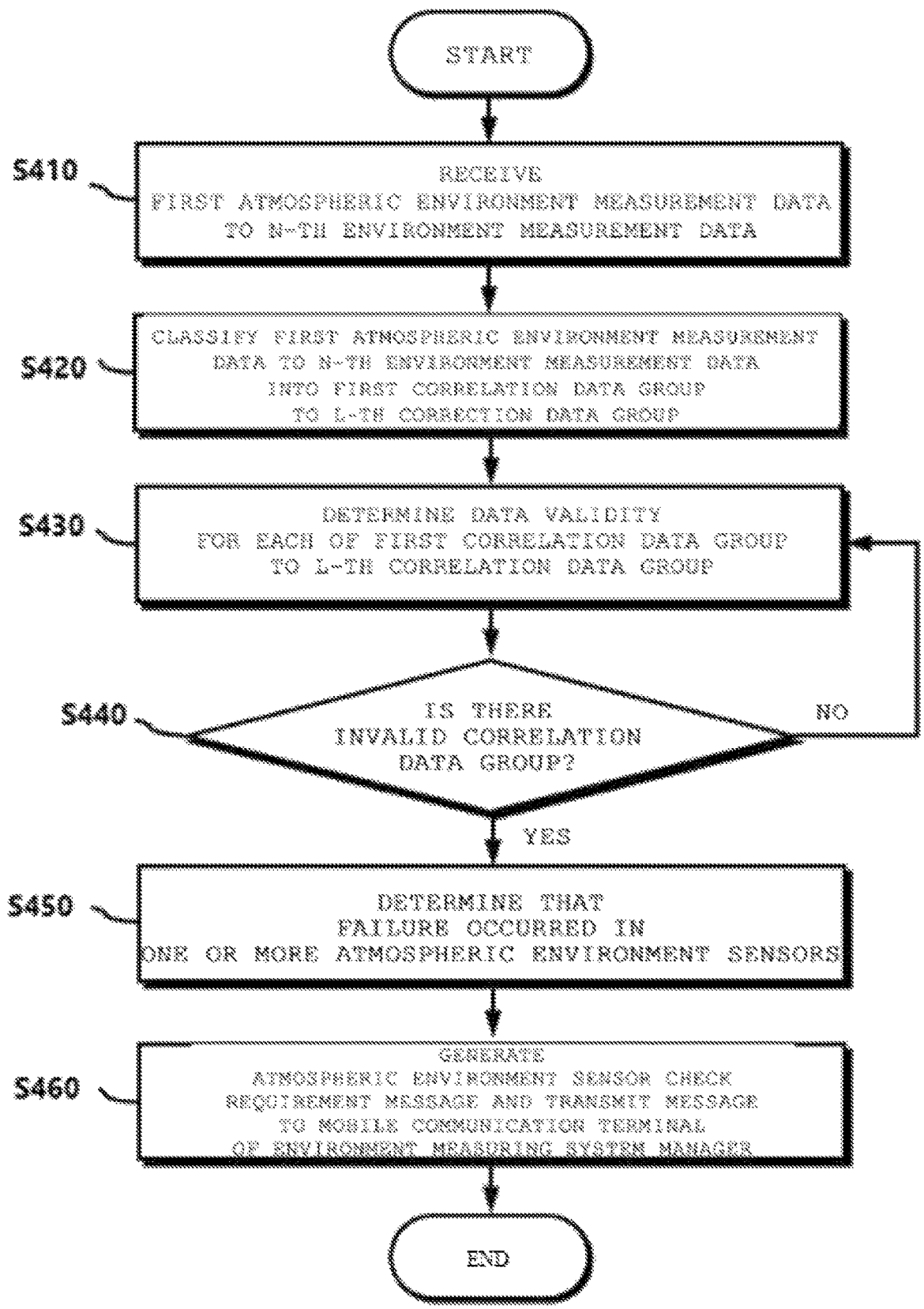
FIG. 4 is a flowchart illustrating a process in which an atmospheric environment monitoring apparatus according to a second embodiment of the invention detects failure of an atmospheric environment sensor.

FIG. 4 is a flowchart illustrating a process in which an atmospheric environment monitoring apparatus according to the second embodiment of the invention detects failure of an atmospheric environment sensor.

First, an atmospheric environment monitoring apparatus 120 periodically receives first atmospheric environment measurement data to N-th atmospheric environment measurement data from a first atmospheric environment sensor to an N-th atmospheric environment sensor 110 (S410).

Thereafter, the atmospheric environment monitoring apparatus 120 classifies the first atmospheric environment measurement data to the N-th atmospheric environment measurement data received from the first atmospheric environment sensor to the N-th atmospheric environment sensor 110 into a first correlation data group to an L-th correlation data group in accordance with correlation to each other (S420).

The atmospheric environment monitoring apparatus 120 which classified the first atmospheric environment measurement data to the N-th atmospheric environment measurement data into the first correlation data group to the L-th correlation data group determines data validity for each of the first correlation data group to the L-th correlation data group (S430).

Specifically, the atmospheric environment monitoring apparatus 120 receives each of two or more atmospheric environment measurement data included in any one correlation data group during a predetermined period, and may identify a data change pattern during a predetermined period for each of two or more atmospheric environment measurement data.

Herein, when the data change patterns for two or more atmospheric environment measurement data are the same, the atmospheric environment monitoring apparatus 120 may determine that two or more atmospheric environment measurement data included in any one correlation data group are valid, that is, may determine that any one correlation data group is valid.

Meanwhile, when there are one or more data change patterns different from the other data change pattern of data change patterns for two or more atmospheric environment measurement data, the atmospheric environment monitoring apparatus 120 may determine that two or more atmospheric environment measurement data included in any one correlation data group are not valid, that is, may determine that any one correlation data group is not valid.

As a result of determination of data validity for each of the first correlation data group to the L-th correlation data group in the atmospheric environment monitoring apparatus 120 by the method described above, when there are one or more invalid correlation data groups of the first correlation data group to the L-th correlation data group, the atmospheric environment monitoring apparatus 120 may determine that failure occurred in one or more atmospheric environment sensors of the first atmospheric environment sensor to the N-th atmospheric environment sensor 110 (S440, S450).

In such a case, the atmospheric environment monitoring apparatus 120 may generate an atmospheric environment sensor check requirement message which is a message for guiding check necessity of the one or more atmospheric environment sensor to an environment measuring system manager, and transmit the message to a mobile communication terminal of the environment measuring system manager (S460).

Meanwhile, in Step S440, when all of the first correlation data group to the L-th correlation data group are valid, the atmospheric environment monitoring apparatus 120 determines that all of the first atmospheric environment sensor to the N-th atmospheric environment sensor 110 are normal, and may perform Step S430 again.

The process in which the atmospheric environment monitoring apparatus 120 detects failure of the atmospheric environment sensor as described above may be embodied by a software program, and the atmospheric environment monitoring apparatus 120 may perform the process by combining with the software program. In other words, the software program is stored and installed in the atmospheric environment monitoring apparatus 120, whereby the atmospheric environment monitoring apparatus 120 performs the process.

According to the embodiment, since it is diversely determined whether failure of an atmospheric environment sensor occurred in the atmospheric environment monitoring apparatus, it is possible to accurately determine failure for each of a plurality of atmospheric environment sensors.

According to the embodiment of the invention, atmospheric environment measurement data received from each of a plurality of atmospheric environment sensors in an atmospheric environment monitoring apparatus are classified into a plurality of data groups in accordance with correlation to each other, data validity is determined by data groups including two or more atmospheric environment data with correlation, and it is possible to determine that failure occurred in one or more atmospheric environment sensors of the plurality of atmospheric environment sensors when there are one or more invalid data groups.

Although it is described above that all constituent elements constituting the embodiments of the invention is combined into one or is operated by combination, the invention is not necessarily limited to such embodiments. In other words, within the scope of the object of the invention, all the constituent elements may be operated by selectively combination into one or more. The above description is merely exemplary description of the technical spirit of the invention, and a person skilled in the art will be able to variously modify and change the invention within the scope which does not deviate from the essential features of the invention. The protection scope of the invention should be interpreted by the following Claims, and it should be interpreted that all the technical spirits within the scope equivalent thereto are included in the scope of rights of the invention.

While the present invention has been described with respect to the specific embodiments, it will be apparent to those skilled in the art that various changes and modifications may be made without departing from the spirit and scope of the invention as defined in the following claims.

What is claimed is:

1. An atmospheric environment monitoring apparatus comprising:
   a communication interface unit which periodically receives first atmospheric environment measurement data to N-th atmospheric environment measurement data from a first atmospheric environment sensor to an N-th atmospheric environment sensor;
   a data storage unit which cumulates and stores the first atmospheric environment measurement data to the N-th atmospheric environment measurement data periodically received from the first atmospheric environment sensor to the N-th atmospheric environment sensor by the communication interface unit; and a control unit which classifies the first atmospheric environment measurement data to the N-th atmospheric environment measurement data into a first correlation data group to an L-th correlation data group, determines data validity for each of the first correlation data group to the L-th correlation data group, and determines that failure occurred in one or more atmospheric environment sensors of the first atmospheric environment sensor to the N-th atmospheric environment sensor when there are one or more invalid correlation data groups of the first correlation data group to the L-th correlation data group, wherein the control unit determines failure occurrence of one or more atmospheric environment sensors, generates an atmospheric environment sensor check requirement message which is a message for guiding check necessity of the one or more atmospheric environment sensors, and transmits the atmospheric environment sensor check requirement message to a mobile communication terminal of the environment measuring system manager through the communication interface unit.

2. The atmospheric environment monitoring apparatus according to claim 1, wherein the control unit extracts two or more atmospheric environment measurement data included in any one correlation data group of the first atmospheric environment measurement data to the N-th atmospheric environment measurement data stored in the data storage unit, identifies a data change pattern during a predetermined period for each of the two or more atmospheric environment measurement data, determines that the correlation data group is valid when the data change patterns for the two or more atmospheric environment measurement data are the same, and determines that the correlation data group is not valid when there are one or more data change patterns different from the other data change pattern of the data change patterns for each of the two or more atmospheric environment measurement data.

3. The atmospheric environment monitoring apparatus according to claim 1, wherein the first atmospheric environment measurement data to the N-th atmospheric environment measurement data include VOC (volatile organic compound), carbon monoxide concentration data, carbon dioxide concentration data, and fine dust concentration data, and the control unit classifies the carbon monoxide concentration data and the carbon dioxide concentration data having a proportional relation to each other into a first correlation data group, and classifies the VOC concentration data and the fine dust concentration data into a second correlation data group.

4. A method for detecting failure of an atmospheric environment sensor in an atmospheric environment monitoring apparatus, comprising:
a data reception step of periodically receiving first atmospheric environment measurement data to N-th atmospheric environment measurement data from a first atmospheric environment sensor to an N-th atmospheric environment sensor;

a data classification step of classifying the first atmospheric environment measurement data to the N-th atmospheric environment measurement data into a first correlation data group to an L-th correlation data group in accordance with correlation to each other;

a validity determination step of determining data validity for each of the first correlation data group to the L-th correlation data group;

a sensor failure detection step of determining that failure occurred in one or more atmospheric environment sensors of the first atmospheric environment sensor to the N-th atmospheric environment sensor when there are one or more invalid correlation data groups of the first correlation data group to the L-th correlation data group, as a result of determination of data validity for each of the first correlation data group to the L-th correlation data group; and after the sensor failure detection step, a sensor failure guide step of generating an atmospheric environment sensor check requirement message which is a message for guiding check necessity of the one or more atmospheric environment sensors to an environment measuring system manager, and transmitting the message to a mobile communication terminal of the environment measuring system manager.

5. The method for detecting failure of an atmospheric environment sensor in an atmospheric environment monitoring apparatus according to claim 4, wherein the validity determination step includes
a step of receiving each of two or more atmospheric environment measurement data included in any one correlation data group for a predetermined period, and identifying a data change pattern during a predetermined period for each of the two or more atmospheric environment measurement data, a step of determining that the correlation data group is valid when the data change patterns for the two or more atmospheric environment measurement data are the same, and a step of determining that the correlation data group is not valid when there are one or more data change patterns different from the other data change pattern of the data change patterns for each of the two or more atmospheric environment measurement data.

6. The method for detecting failure of an atmospheric environment sensor in an atmospheric environment monitoring apparatus according to claim 4, wherein in the data classification step, the first atmospheric environment measurement data to the N-th atmospheric environment measurement data include VOC (volatile organic compound), carbon monoxide concentration data, carbon dioxide concentration data, and fine dust concentration data, and the atmospheric environment monitoring apparatus classifies the carbon monoxide concentration data and the carbon dioxide concentration data having a proportional relation to each other into a first correlation data group, and classifies the VOC concentration data and the fine dust concentration data into a second correlation data group.

* * * * *